(12) United States Patent
Emerit et al.

(10) Patent No.: US 6,595,969 B1
(45) Date of Patent: Jul. 22, 2003

(54) CUTANEOUS APPLICATOR WITH A LIQUID STORAGE CARTRIDGE

(76) Inventors: Michel Emerit, 33, rue d'Alsace, Sannois (FR), 95110; Yanick Paternotte, 10, avenue Rozée, Sannois (FR), 95110

(*) Notice: Subject to any disclaimer, the term of this patent is extended or adjusted under 35 U.S.C. 154(b) by 0 days.

(21) Appl. No.: 09/979,095
(22) PCT Filed: May 12, 2000
(86) PCT No.: PCT/FR00/01298
§ 371 (c)(1), (2), (4) Date: Nov. 19, 2001
(87) PCT Pub. No.: WO00/71198
PCT Pub. Date: Nov. 30, 2000

(30) Foreign Application Priority Data

May 21, 1999 (FR) .............................. 99 06519

(51) Int. Cl.[7] .............................................. A61M 35/00
(52) U.S. Cl. ...................................... 604/289; 401/266
(58) Field of Search ................. 604/1, 289, 290; 401/266, 261, 23, 25, 26, 132–134, 139, 196, 202–205; 222/541.1

(56) References Cited

U.S. PATENT DOCUMENTS

| 314,840 | A | * | 3/1885 | Gilchrist et al. ........... 24/713.4 |
| 4,913,682 | A | | 4/1990 | Shabo |
| 6,299,377 | B1 | * | 10/2001 | Emerit et al. ............. 222/541.1 |

FOREIGN PATENT DOCUMENTS

| EP | 0 320 131 | 6/1989 |
| FR | 2 770 410 | 5/1999 |
| WO | 96/40445 | 12/1996 |

* cited by examiner

Primary Examiner—Weilun Lo
Assistant Examiner—Linh Truong
(74) Attorney, Agent, or Firm—Wenderoth, Lind & Ponack, L.L.P.

(57) ABSTRACT

A cutaneous applicator (10) for a liquid including a liquid storage cartridge (16) which is provided with an outlet (22) for the evacuation of the liquid. Also provided is a hydrophilic pledget (12) for applying the liquid to an area which is to be treated, and a structure (14) for maintaining the hydrophilic pledget (12) in a position opposite to the outlet for the evacuation of the liquid from the cartridge (16). The structure (14) for maintaining the pledget is integral with the cartridge (16). The applicator can be used to apply an aseptic liquid for cutaneous treatment.

20 Claims, 3 Drawing Sheets

CUTANEOUS APPLICATOR WITH A LIQUID STORAGE CARTRIDGE

BACKGROUND OF THE INVENTION

1. Field of the Invention

The present invention relates to a cutaneous applicator for liquid, of the type comprising a storage cartridge for the liquid which is provided with an outlet for evacuation of the liquid, a hydrophilic pledget for applying liquid to an area which is to be treated, and means for maintaining the hydrophilic pledget opposite an outlet for evacuation of the liquid from the cartridge.

2. Description of Related Art

It is commonplace to use a hydrophilic pledget for applying a disinfectant liquid or a medicinal substance to a wound.

In order to prevent too rapid drying of the hydrophilic pledget during its storage, it is commonplace to store the hydrophilic pledget and the liquid for impregnating the pledget separately.

For example, document WO-91/12197 describes a cutaneous application device comprising a storage cartridge to which a head for applying the liquid is attached. The application head comprises a carrying structure on which a hydrophilic pledget is mounted. The application head is manufactured separately from the cartridge, and then mounted on the latter using mechanical coupling means such as snap-fit means. In order to allow opening of the cartridge, at least a portion of the carrying structure is mounted so as to be displaceable.

Therefore, the application head has a relatively complex structure, considerably increasing the cost of the cutaneous applicator.

SUMMARY OF THE INVENTION

The object of the invention is to propose a cutaneous applicator whose cost of manufacture is low, whilst still allowing the liquid which is to be applied, to be initially confined in a storage cartridge.

To this end, the subject of the invention is a cutaneous applicator for liquid of the above-mentioned type, characterized in that the means for maintaining the pledget are integral with the cartridge.

According to particular embodiments, the applicator comprises one or a number of the following characteristics:

(1) the maintaining means comprise an arch for supporting the pledget surmounting the outlet for evacuation of the liquid from the cartridge, the arch being integral at its ends with the cartridge;

(2) the cartridge comprises a body for storing the liquid which is extended by a neck of small cross section, delimiting a conduit for conveying the liquid as far as the evacuation outlet, and the arch is connected to the cartridge at the base of the neck;

(3) the neck comprises at least one longitudinal reinforcement rib;

(4) the cartridge is an initially hermetically sealed cartridge, of which the opening for evacuation of the liquid is closed off by a releasable stopper, and the maintaining means are deformable elastically between a rest position and a position of release of the stopper;

(5) the cartridge comprises a closing-off stopper which can be dried through the action of angular displacement relative to the axis of the cartridge, and the arch comprises lateral legs which are connected, at their ends, to the cartridge, the legs being deformable elastically in the form of a helix in order to allow the arch to be twisted;

(6) the stopper is separate from the arch and comprises at least one actuation projection;

(7) the stopper is integral with the arch for its angular displacement relative to the body upon elastic deformation of the arch;

(8) it comprises a member for perforating the closing-off stopper, this member being carried by the arch and arranged opposite the opening;

(9) the perforation member is carried by a transverse bridge provided at the ends of two lateral legs of the arch, the other ends of the legs being connected to the cartridge, and the bridge is deformable elastically by flexion toward the opening of the cartridge; and

(10) the hydrophilic pledget comprises a hydrophilic strip which is folded over on itself, and the maintaining means are adapted for maintaining the outlet for evacuation from the cartridge fitted between the folded-over edges of the strip.

BRIEF DESCRIPTION OF THE DRAWINGS

The invention will be better understood upon reading the following description which is given solely by way of example and refers to the drawings, in which.

DETAILED DESCRIPTION OF THE INVENTION

Figure 1:
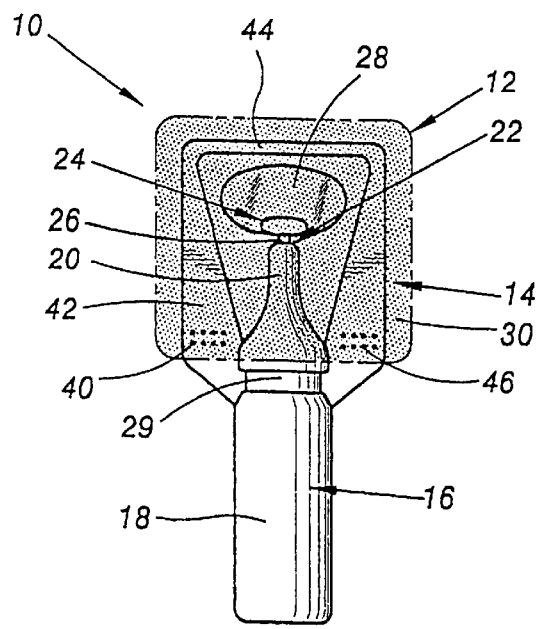
FIGS. 1 and 2 are views in elevation, of the front and of the side, respectively, of a cutaneous applicator according to the invention.
Figure 2:
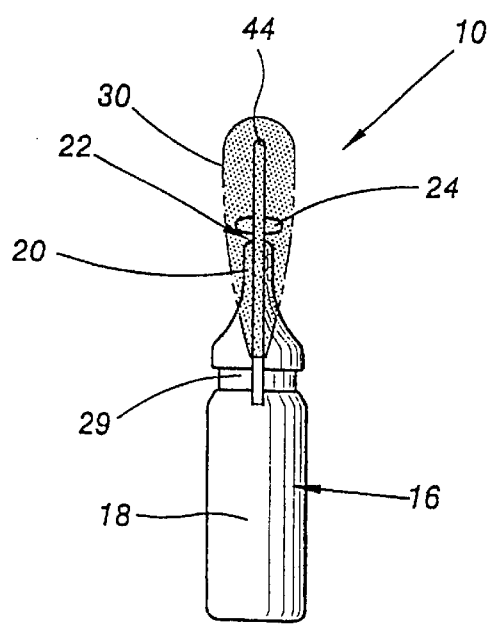
Figure 3:
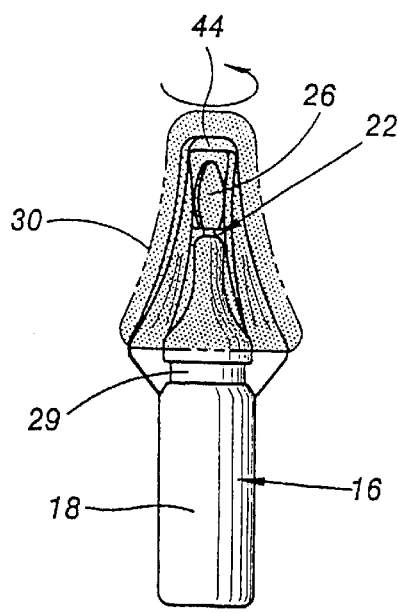
FIG. 3 is a view in elevation of the front of the cutaneous applicator show in FIGS. 1 and 2, shown during opening of the cartridge.

FIGS. 1 to 3 show a cutaneous applicator 10 comprising a hydrophilic pledget 12 retained by maintaining means 14 on a cartridge 16 for storing an aseptic active liquid. This liquid is, for example, a disinfectant or a medicinal substance.

The cartridge 16 is made from molded plastic. It is produced by pressing, between two half-molds, a tube of polymer obtained at the outlet from an extruder. During pressing, the polymer tube is maintained under pressure by air being blown through it.

The cartridge comprises a substantially cylindrical flexible body 18. The body is extended in its upper part by a throat or neck 20 having an outer cross section which grows progressively smaller toward its free end. The neck 20 delimits, on the inside, a conduit for conveying the liquid as far as an axial outlet 22. Initially, the outlet 22 is closed off by a dryable stopper 24, which is integral with the neck 20.

The stopper 24 is connected to the end of the neck in order to close off the outlet 22 by means of a breakable tip 26 which allows detachment of the stopper 24 and opening of the cartridge, by angular displacement of the stopper relative to the body of the cartridge.

For this purpose, the stopper 24 is integral with an actuating projection 28 consisting, for example, of a tongue in the form of an ellipse which is integral with the stopper.

At the base of the neck 20, the body 18 of the cartridge has a peripheral groove 29.

The capacity of the cartridge is adapted to contain the amount of liquid required for a single use. This capacity is between 1 ml and 5 ml and is, for example, equal to 2.5 ml, without these values being regarded as limitative.

In the applicator 10 shown in FIGS. 1 to 3, a hydrophilic pledget 12 is retained by the maintaining means 14 on the storage cartridge opposite the outlet 22 for evacuation of the liquid from the cartridge. The pledget 12 is formed from a hydrophilic strip 30, for example a strip of gauze.

The hydrophilic strip 30 is folded around the maintaining means 14 so that the outlet 22 for evacuation from the cartridge is fitted between the two folded-down edges of the hydrophilic strip 30.

To this end, the maintaining means 14 comprise an arch 40 that is integral at its ends with the cartridge 16. The arch 40, which has the general shape of a U, surmounts the evacuation outlet 22 and the stopper 24.

The arch 40 comprises two lateral legs 42 connected to one another by a transverse bridge 44 surmounting the evacuation outlet 22. The arch 40 delimits an arc inside which the neck 20, the stopper 24 and the tongue 28 initially extend. The stopper 24 and the tongue 28 are separated from the arch 40 by a peripheral gap. The legs 42 are connected at one of their ends, laterally on either side of the body 18 in the upper region of the latter where the groove 29 is provided. The legs 42 extend in the median longitudinal plane of the cartridge. The two legs 42 and the bridge 44 are integral with the cartridge.

To produce the arch 40, the two half-molds adapted for manufacturing the cartridge 16 comprise, in the upper part of the impression delimiting the cartridge, generally U-shaped channels delimiting the shape of the arch 40. Thus, when the two half-molds are in contact, the two opposite walls of the polymer tube are compressed against one another in the U-shaped channels, thus forming the arch 40.

Moreover, when the two half-molds are brought together, they are not applied in complete contact with one another so that a web is formed all around the cartridge 18 and the arch 40, and inside the zone delimited by the arch 40.

After demolding of the cartridge, this web is removed by being cut along the outer contour of the cartridge 18 and the arch 40, and by cutting the web inside the zone delimited by the arch 40, along the inner periphery thereof. This cut is advantageously made by a punching tool.

As shown, the width of the legs 42 decreases progressively from the body 18 of the cartridge as far as the transverse bridge 44. The bridge 44 constitutes a support for the hairpin-bend-shaped end of the hydrophilic strip 30.

Moreover, at the base of the legs 42, i.e. at their end which connects with the cartridge, points 46 for securing the hydrophilic strip 30 are provided on the two opposite faces of the legs. These points are adapted to penetrate through the porous structure of the hydrophilic strip in order to be embedded therein and thus to weld the folded-down ends of the strip onto the maintaining means 14.

As illustrated in FIG. 3, the legs 42 are of a size to allow their elastic deformation into a helical profile in order to permit angular deflection of the bridge 44 during manual entrainment thereof.

Thus, the arch may be deformed by twisting about the longitudinal axis of the cartridge.

The maintaining means 14 are thus deformable elastically between a rest position shown in FIG. 2, in which the arch is flat, and a sectioning position of the stopper 24, shown in FIG. 3, in which the legs 42 of the arch are deformed in the form of a helix, whereas the stopper 24 is detached by shearing.

It will in fact be understood that, as the body of the cartridge is held between the fingers, a rotary movement of the hydrophilic pledget 12 about the axis of the cartridge 16, through the action of the fingers stressing the free end of the pledget, gives rise to the shearing of the stopper 24 and thus opening of the cartridge. During deformation of the hydrophilic pledget and of the arch by twisting, the tongue 28 is simultaneously stressed, which leads to breakage of the tip 26 connecting the stopper 24 to the neck.

After detachment of the stopper, the liquid contained in the cartridge is free to flow, in order to impregnate the hydrophilic strip, particularly through the action of manual pressure exerted on the flexible body of the cartridge.

The pledget being thus impregnated, the user can dab the area which is to be treated with the pledget while holding only the body of the cartridge.

It will be understood that as the means 14 for maintaining the hydrophilic strip are integral with the cartridge, they are very inexpensive to manufacture as they are produced simultaneously with manufacture of the cartridge.

The following figures show variant embodiments of the applicator according to the invention.

In these Figures, elements which are identical or similar to those in FIGS. 1 to 3 are denoted by the same reference numerals.

Figure 4:
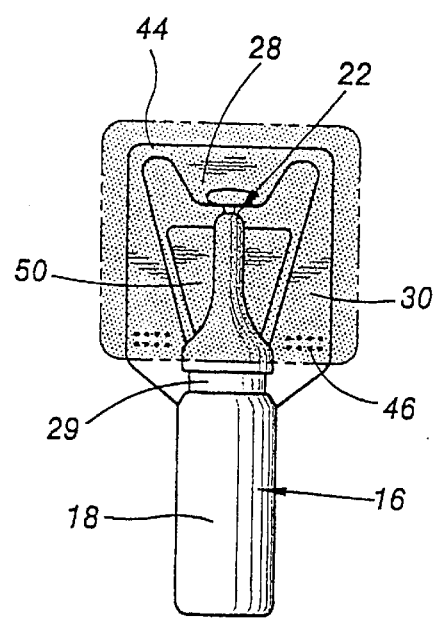
FIGS. 4 and 5 are views in elevation of variant embodiments of a cutaneous applicator according to the invention.

In the embodiment shown in FIG. 4, the tongue 28 for actuating the stopper 24 is integral with the bridge 44. Thus, during rotation entrainment of the arch 40, the stopper 24 is sheared, even if the operator applies his fingers only to the bridge 44. Moreover, in this embodiment, the neck 20 comprises, longitudinally, reinforcement ribs 50 arranged longitudinally on either side of the arch 40.

Figure 5:
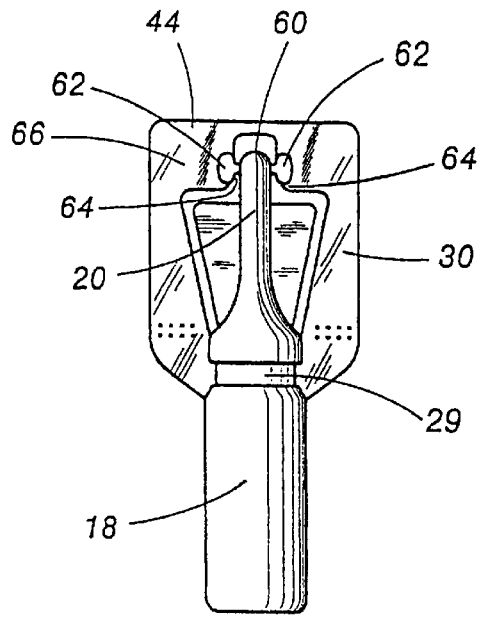

For reasons of clarity concerning the drawings, the hydrophilic strip 30 is not shown in FIGS. 5 etc.

In the embodiment shown in FIG. 5, the neck 20 is closed off axially by an end wall 60 which cannot be dried. On the other hand, the neck is provided, at its free end, with two lateral evacuation outlets which are diametrically opposed and arranged in the plane of the arch 40. These evacuation outlets are closed off by stoppers 62 integral with the neck and connected to the latter by breakable tips 64 extending radially relative to the axis of the neck.

The stoppers 62 are connected to the bridge 44 of the arch by extensions 66 provided in the angle delimited between the legs 42 and the bridge 44.

In this embodiment, also, it will be understood that, upon angular displacement of the bridge 44 relative to the cartridge 16 about the axis of the latter, the stoppers 62 are entrained, giving rise to the breakage of the breakable tips 64 and thus opening of the outlets for evacuation of the liquid.

Figure 6:
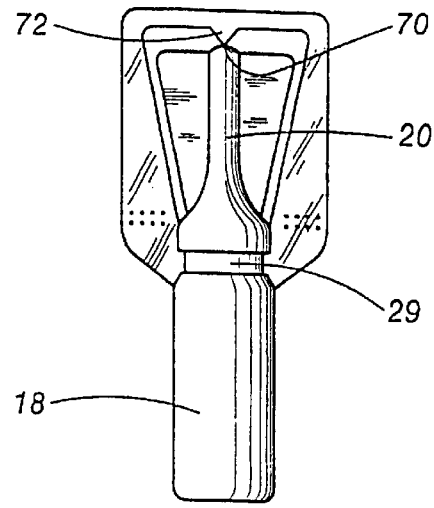
FIGS. 6 and 7 are views in elevation of the same embodiment of a cutaneous applicator according to the invention, shown before opening and during opening, respectively, of the outlet for evacuation of the liquid.
Figure 7:
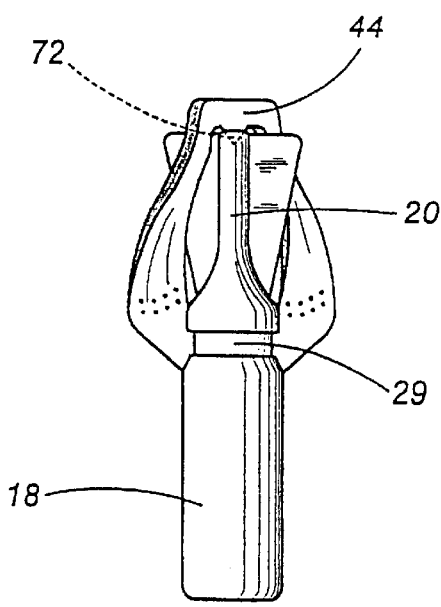
Figure 8:
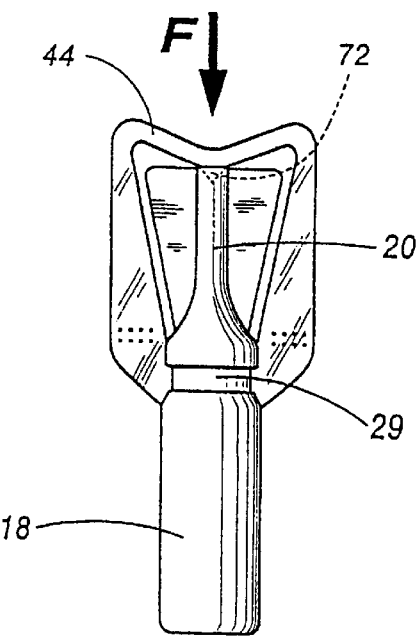
FIG. 8 is a view in elevation of a variant embodiment of a cutaneous applicator according to the invention, shown during its opening.

In the embodiments in FIGS. 6 to 8, the neck 20 of the cartridge is closed off axially by a pierceable capsule 70, which forms a releasable stopper. Opposite the pierceable capsule 70 there is initially a perforation member 72 carried by the bridge 44. This perforation member is advantageously integral with the bridge 44 and consists of a spike extending in the axis of the neck 20. The pointed end of the perforation member 72 is initially arranged in the immediate vicinity of the capsule 70.

In the embodiment of FIGS. 6 and 7, the legs 42 of the arch are deformable elastically in the form of a helix, as in the previous embodiments. Thus, in order to proceed with opening the cartridge, and as illustrated in FIG. 7, the operator displaces the bridge 44 angularly relative to the cartridge, thus giving rise to the deformation of the legs.

During this deformation, the spike 72 undergoes, on the one hand, a rotational movement about the axis of the cartridge, and, on the other hand, an axial displacement toward the neck 20, due to the deformation of the legs 42 of constant length in the form of a helix.

Thus, the spike 72 pierces the capsule 70 and opens the cartridge.

In the embodiment shown in FIG. 8, the bridge 44 has, as in the preceding embodiment, a perforation member 72.

However, in this embodiment, the legs of the arch are rigid. Nevertheless, the bridge 44 is deformable elastically by flexion upon application of an axial thrust, as illustrated by the arrow F.

Thus, when the operator applies a pressure in the direction of the arrow F, the perforation member 72 penetrates the evacuation passage delimited by the neck 20 and breaks the capsule 70, thus allowing release of the liquid contained in the cartridge.

Figure 9:
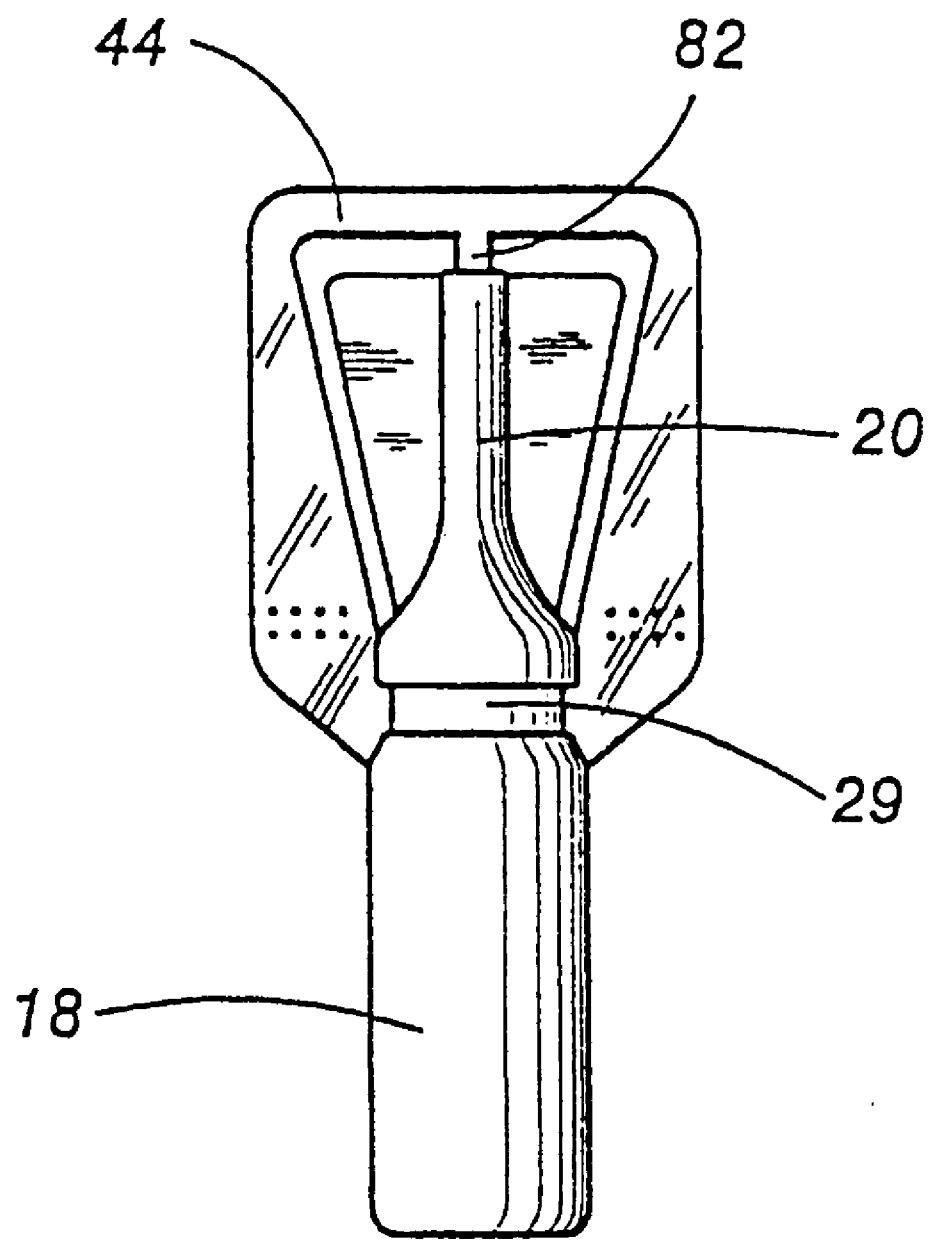
FIG. 9 is a view in elevation of a further embodiment of a cutaneous applicator according to the invention.

In the embodiment shown in FIG. 9, the bridge 44 is connected to the end of the neck 20 by a tip 82 forming the stopper and closing off the evacuation conduit delimited by the neck 20. The tip 82 is integral with the neck 20 and the tip 44.

In this embodiment, the cartridge is opened by rotation of the bridge 44 about the axis of the cartridge. This rotation gives rise to the breakage of the link between the tip 82 and the end of the neck 20, thus opening the cartridge 16.

Moreover, opening may also be obtained by axial pressure on the bridge 44, in order temporarily to press the tip 82 into the neck 20, thus opening the cartridge.

What is claimed is:

1. A cutaneous applicator for liquid, said applicator comprising:
    a liquid storage cartridge for storing the liquid, said cartridge being provided with an outlet for evacuation of the liquid;
    a hydrophilic pledget for applying liquid to an area which is to be treated; and
    means for maintaining said hydrophilic pledget opposite said outlet for evacuation of the liquid from said cartridge, wherein said means for maintaining the pledget is integral with said cartridge, and
    wherein said means for maintaining comprises an arch for supporting the pledget, said arch surmounting said outlet for evacuation of the liquid from said cartridge, and said arch is integral at its ends with said cartridge.

2. The cutaneous applicator as claimed in claim 1, wherein said cartridge comprises a body for storing the liquid, and a neck extending from said body to said outlet, said neck defining a conduit for conveying the liquid to said outlet, and said arch is connected to said cartridge at a base of said neck.

3. The applicator as claimed in claim 1, wherein said cartridge comprises a closing-off stopper, which can be removed through angular displacement relative to the axis of said cartridge,
    wherein said arch comprises lateral legs connected at their first ends to said cartridge, said legs being elastically deformable in the form of a helix in order to allow said arch to be twisted.

4. The cutaneous applicator as claimed in claim 3, wherein said neck comprises at least one longitudinal reinforcement rib.

5. The cutaneous applicator as claimed in claim 1, wherein said cartridge is an initially hermetically sealed cartridge, and said outlet is closed by a stopper, and said means for maintaining is elastically deformable between a rest position and a position of releasing said stopper.

6. The applicator as claimed in claim 1, wherein said cartridge comprises a closing-off stopper, which can be removed through angular displacement relative to the axis of said cartridge,
    wherein said arch comprises lateral legs connected at their first ends to said cartridge, said legs being elastically deformable in the form of a helix in order to allow said arch to be twisted.

7. The applicator as claimed in claim 6, wherein said stopper is separate from said arch and comprises a least one actuation projection.

8. The applicator as claimed in claim 6, wherein said stopper is integral with said arch so that it will be angularly displaced upon elastic deformation of said arch.

9. The applicator as claimed in claim 5, further comprising a perforating member for perforating said closing-off stopper, said perforating member being carried by said arch and arranged opposite said outlet.

10. The applicator as claimed in claim 1, wherein said cartridge comprises a body for storing the liquid, and a neck extending from said body to said outlet, said neck defining a conduit for conveying the liquid to said outlet, and said conduit is initially closed by a closing-off stopper,
    wherein said applicator further comprises a member for perforating said closing-off stopper, and said member is carried by said arch and is arranged so as to oppose said outlet.

11. The applicator as claimed in claim 10, wherein said arch comprises a transverse bridge and a pair of lateral legs each of which has a first end connected to said cartridge, and a second end connected to said transverse bridge, and wherein said perforation member is carried by said transverse bridge.

12. The applicator as claimed in claim 11, wherein said bridge is elastically deformable.

13. The applicator as claimed in claim 1, wherein said hydrophilic pledget comprises a hydrophilic strip which is folded over on itself, and said arch is adapted to maintain said outlet fitted between the folded-over edges of said hydrophilic strip.

14. A liquid applicator comprising:
    a liquid storage cartridge having an outlet and a stopper blocking the outlet;
    a hydrophilic pledget for applying liquid to an area to be treated; and
    an elastically deformable U-shaped structure for supporting said hydrophilic pledget, said U-shaped structure comprising a first leg having first and second ends, a second leg having first and second ends, and a transverse member connected to the first end of said first leg and the first end of said second leg,
    wherein said transverse member extends over said outlet, and the second ends of said first and second legs are integrally connected to said cartridge.

15. The liquid applicator as claimed in claim 14, further comprising an actuating projection connected to said stopper.

16. The liquid applicator as claimed in claim 15, wherein said stopper includes a breakable tip which permits detachment of said stopper and opening of the cartridge upon deforming said U-shaped structure into the shape of a helix.

17. The liquid applicator as claimed in claim 14, wherein said cartridge comprises a cartridge body and a neck defining a liquid passage, and said stopper comprises an end wall of said neck.

18. The liquid applicator as claimed in claim 17, further comprising a perforation member carried by said transverse member and positioned so as to be opposed to the outlet.

19. The liquid applicator as claimed in claim 14, wherein said transverse member is integrally connected to said stopper.

20. A liquid applicator comprising:
  a liquid storage cartridge having a cartridge body and a neck defining a liquid passage terminating in two lateral evacuation outlets which are diametrically opposed to each other;
  a first stopper having a breakable tip closing one of said outlets;
  a second stopper having a breakable tip closing the other of said outlets, wherein said first and second stoppers are integral with said neck;
  a hydrophilic pledget for applying liquid to an area to be treated; and
  an elastically deformable U-shaped structure for supporting said hydrophilic pledget, said U-shaped structure comprising a first leg having first and second ends, a second leg having first and second ends, and a transverse member connected to the first end of said first leg and the first end of said second leg,
  wherein said transverse member extends over said neck, and said first and second stoppers are connected to said transverse member.

* * * * *